United States Patent [19]

Sato et al.

[11] Patent Number: 4,945,105
[45] Date of Patent: Jul. 31, 1990

[54] 13-HALOMILBEMYCIN DERIVATIVES, THEIR PREPARATION AND COMPOSITIONS CONTAINING THEM

[75] Inventors: Kazuo Sato; Toshiaki Yanai; Noritoshi Kitano, all of Tokyo; Akira Nishida, Shiga, all of Japan; Bruno Frei, Liestal; Anthony O'Sullivan, Basel, both of Switzerland

[73] Assignee: Sankyo Company Limited, Tokyo, Japan

[21] Appl. No.: 290,835

[22] Filed: Dec. 28, 1988

Related U.S. Application Data

[63] Continuation of Ser. No. 866,571, May 22, 1986, abandoned.

[30] Foreign Application Priority Data

May 31, 1985 [JP] Japan .................................. 60-118629

[51] Int. Cl.$^5$ ................... A61K 31/364; C07D 313/00
[52] U.S. Cl. .................................... 514/450; 549/264; 549/214; 536/7.1; 514/30; 514/63
[58] Field of Search ................ 549/264, 214; 514/450, 514/30, 63; 536/7.1

[56] References Cited

U.S. PATENT DOCUMENTS

| | | | |
|---|---|---|---|
| Re. 32,034 | 11/1985 | Chabala et al. | 549/264 |
| 3,950,360 | 4/1976 | Aoki et al. | 549/264 |
| 4,134,973 | 1/1979 | Fisher et al. | 514/30 |
| 4,156,720 | 5/1979 | Fisher et al. | 514/30 |
| 4,173,571 | 11/1979 | Chabala et al. | 549/264 |
| 4,346,171 | 8/1982 | Takiguchi et al. | 549/264 |
| 4,423,209 | 12/1983 | Mrozik | 536/7.1 |
| 4,547,520 | 10/1985 | Ide et al. | 549/264 |

OTHER PUBLICATIONS

H. Mrozik et al, Tetrahedron Letters, vol. 24(48) (1983), pp. 53333–53336.

*Primary Examiner*—Richard L. Raymond
*Assistant Examiner*—Mark W. Russell
*Attorney, Agent, or Firm*—Frishauf, Holtz, Goodman & Woodward

[57] ABSTRACT

Derivatives of milbemycins D, $A_3$ and $A_4$ and of the corresponding sec-butyl compound have a halogen atom at the 13-position; at the 5-position, they have an oxygen (keto) atom, an oxime group or a substituted oxime group. They may be prepared from known compounds by any appropriate combination of halogenation, ketonization and oximation.

54 Claims, No Drawings

13-HALOMILBEMYCIN DERIVATIVES, THEIR PREPARATION AND COMPOSITIONS CONTAINING THEM

This application is a continuation, of application Ser. No. 06/866,571, filed May 22, 1986 now abandoned.

BACKGROUND TO THE INVENTION

The present invention relates to a series of new derivatives of the compounds known as "milbemycins", particularly of miblemycin $A_3$, milbemycin $A_4$, milbemycin D and of the corresponding compound having a sec-butyl group at the 25-position.

The milbemycins are a series of macrolide compounds known to have anthelmintic, acaricidal and insecticidal activities. Milbemycin D was disclosed in U.S. Pat. No. 4,346,171, where it was referred to as "compound B-41D", and milbemycins $A_3$ and $A_4$ were disclosed in U.S. Pat. No. 3,950,360. These compounds may be represented by the formula (A):

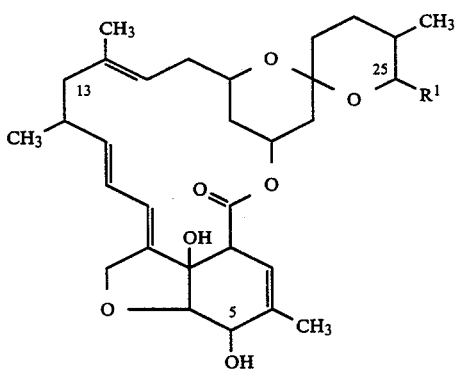

in which $R^1$ represents a methyl group, an ethyl group or an isopropyl group, these compounds being milbemycin $A_3$, milbemycin $A_4$ and milbemycin D, respectively. For the avoidance of doubt, formula (A) also shows the numbering applied to the positions most relevant to the compounds of the present invention.

These milbemycin compounds may be isolated from cultures of the Streptomyces strain B-41-146, which has been deposited at the Fermentation Research Institute, Agency of Industrial Science and Technology, Ministry of International Trade and Industry, Japan, whence it is available under the accession number FERM-1438. The compounds have been found to have valuable anthelmintic and acaricidal activities.

Subsequently, other derivatives of the milbemycins, primarily by substitution at the 5-position and/or the 13-position, have been discovered, and some of these have shown potentially valuable anthelmintic and/or acaricidal and/or insecticidal activities. For example, U.S. Pat. No. 4,093,629 discloses certain 13-bromo derivatives, and 13-halo derivatives more generally are disclosed in U.S. Pat. No. 4,173,571. Closer to the present invention are the 5-ketomilbemycin derivatives [i.e. similar to formula (A) but the hydroxy group and the hydrogen atom at the 5-position are replaced by an oxygen, =O, atom] disclosed in U.S. Pat. No. 4,423,209 and their 5-oxime derivatives [i.e. formula (A) but the hydroxy group and hydrogen atom at the 5-position are replaced by a group of formula =N—OH], as disclosed in U.S. Pat. No. 4,547,520; however, unlike the compounds of the invention but like their parent milbemycins, most of these compounds are unsubstituted at the 13-position; only the compounds of U.S. Pat. No. 4,423,209 have a 13-hydroxy substituent.

A 13-halomilbemycin derivative is disclosed in Tetrahedron Letters, 24 (48), 5333–5336, but no biological activity is disclosed for the compound.

We have now discovered a series of 13-halo derivatives of the 5-ketomilbemycins and their oximes which have demonstrated, in certain test systems, activities, particularly acaricidal activities, far better than the corresponding activities of their parent compounds.

BRIEF SUMMARY OF INVENTION

The compounds of the invention are 13-halo derivatives of 5-ketomilbemycins and their oximes, and may be represented by the formula (I):

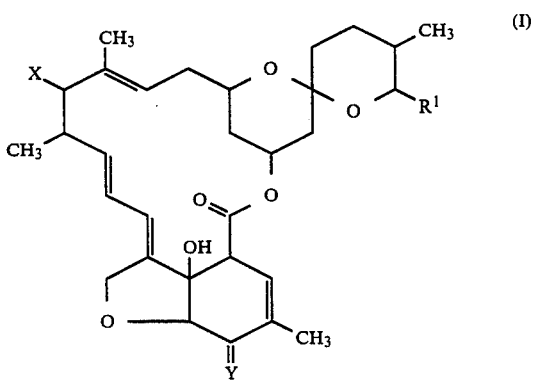

in which:

$R^1$ represents a methyl group, an ethyl group, an isopropyl group or a sec-butyl group;

X represents a halogen atom; and

Y represents an oxygen atom or a group of formula =N—OR$^2$, wherein $R^2$ represents a hydrogen atom, a $C_1$–$C_6$ alkyl group, a $C_7$–$C_9$ aralkyl group, a $C_7$–$C_9$ aralkyl group having at least one substituent selected from the group consisting of $C_1$–$C_6$ alkyl, halogen and nitro substituents or a group of formula —CH$_2$COOR$^3$, in which $R^3$ represents a hydrogen atom or a $C_1$–$C_6$ alkyl group;

and, where $R^2$ represents a hydrogen atom, salts and esters thereof.

The invention also provides an anthelmintic, acaricidal and insecticidal composition comprising an anthelmintic, acaricidal and insecticidal compound in admixture with a pharmaceutically, agriculturally or horticulturally acceptable carrier or diluent, wherein the compound is selected from compounds of formula (I), their salts, their esters and mixtures thereof.

The invention still further provides a method of treating an animal, which may be human or non-human, parasitized by a parasite selected from helminths, acarids and insects, which comprises applying to or administering to said animal an active compound, wherein said active compound is selected from compounds of formula (I), their salts, their esters and mixtures thereof.

The invention still further provides a method of protecting animals or plants from damage by parasites selected from the group consisting of acarids, helminths and insects, which comprises applying an active compound to said animals, said plants or to seeds of said plants or to a locus including the same, wherein the active compound is selected from compounds of formula (I), their salts, their esters and mixtures thereof.

DETAILED DESCRIPTION OF INVENTION

The compounds of the invention are characterized by a halogen atom, X, at the 13-position. It may be a fluorine, chlorine, bromine or iodine atom, preferably a chlorine or fluorine atom.

In the compounds of formula (I), where $R^2$ or $R^3$ represents a $C_1$–$C_6$ alkyl group, this may be a straight or branched chain group and is preferably a $C_1$–$C_4$ alkyl group, for example a methyl, ethyl, propyl, isopropyl, butyl, isobutyl or sec-butyl group.

Where $R^2$ represents an optionally substituted aralkyl group, it is preferably a benzyl group, which may be unsubstituted or may have one or more $C_1$–$C_6$ alkyl, halogen or nitro substituents. Examples of $C_1$–$C_6$ alkyl groups which may be substituents on the aralkyl group have been given in relation to $R^2$ and $R^3$, and the preferred alkyl group is the methyl group. Preferred halogen atoms which may be substituents on the aralkyl group are the chlorine and bromine atoms. Examples of optionally substituted aralkyl groups thus include the benzyl, m-methylbenzyl, p-methylbenzyl, p-chlorobenzyl, p-bromobenzyl, p-fluorobenzyl and p-nitrobenzyl groups. The unsubstituted benzyl group is preferred.

A preferred class of compounds of the present invention are those in which $R^2$ represents a hydrogen atom, a $C_1$–$C_6$ alkyl group, a benzyl group or a carboxymethyl group, most preferably a hydrogen atom.

Compounds in which $R^2$ represents a hydrogen atom are oximes and hence can act either as an acid to form salts with a variety of cations, or as a base, to form esters with a variety of acids.

As will be appreciated from the chemical structure, in accordance with the present invention, the biological activities of these salts and esters arise from the 13-halo-5-ketomilbemycin oxime structure rather than from the cations or acids forming, respectively, these salts or esters. Accordingly, there is no particular limitation on the nature of such salts or esters, provided that the activity of such salts and esters is not significantly or unacceptably worse than that of the free compound of formula (I).

In the case of the salts, the compounds of formula (I) may form salts with a variety of metals, particularly alkali metals (such as lithium, sodium or potassium), alkaline earth metals (such as calcium or barium) or other metals (such as magnesium or aluminum), or with certain organic amines, particularly tertiary amines (such as triethylamine or triethanolamine). Of these, the alkali metal salts and particularly the sodium or potassium salts are preferred.

The esters are preferably with a carboxylic acid, a carbamic acid, a carbonic acid, a sulfonic acid or a phosphoric acid and preferred esters are compounds of formula (Ia):

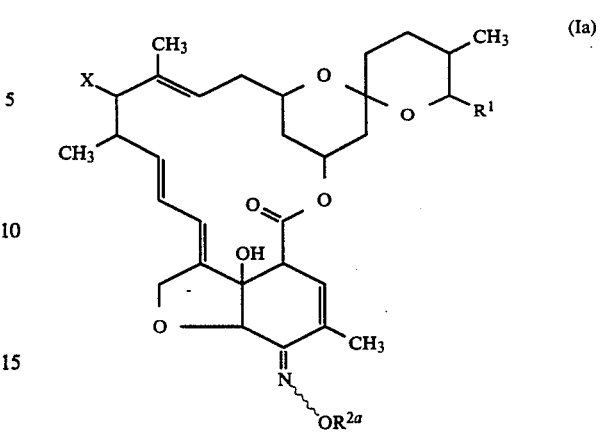

in which $R^1$ and x are as defined above and $R^{2a}$ represents:

A group of formula —$COR^4$, in which $R^4$ represents a $C_1$–$C_{20}$ alkyl group, a $C_2$–$C_{20}$ alkenyl group, a $C_3$–$C_8$ cycloalkyl group, an aralkyl group, an aralkyl group having at least one substituent selected from the group consisting of $C_1$–$C_6$ alkyl, halogen and nitro substituents, a phenyl group, a phenyl group having at least one substituent selected from the group consisting of $C_1$–$C_6$ alkyl, halogen, nitro, carboxy and $C_2$–$C_7$ alkoxycarbonyl substituents or a group of formula —$(CH_2)_n COOR^5$, wherein n is an integer from 1 to 3 and $R^5$ represents a hydrogen atom or a $C_1$–$C_6$ alkyl group;

a group of formula —$CZ.NR^6R^7$, wherein $R^6$ and $R^7$ are the same or different and each represents a hydrogen atom, a $C_1$–$C_6$ alkyl group, a $C_2$–$C_6$ alkenyl group, a $C_2$–$C_6$ alkynyl group or an aryl group and Z represents an oxygen or sulfur atom;

a group of formula —$COOR^8$, wherein $R^8$ represents: a $C_1$–$C_6$ alkyl group; an aralkyl group; an aralkyl group having at least one substituent selected from the group consisting of $C_1$–$C_6$ alkyl, halogen and nitro substituents; an aryl group; a group of formula —$CH_2(-O-CO)_m$—B where m is 0 or 1 and B represents an oxygen-containing heterocyclic group having 5 or 6 ring atoms or said heterocyclic group having at least one $C_1$–$C_4$ alkyl substituent; or a group derived by removing an omega-hydroxy group from a sugar alcohol or protected sugar alcohol;

a group of formula —$SO_2R^9$, wherein $R^9$ represents a $C_1$–$C_6$ alkyl group or an aryl group; or a group of formula —$(Z=)P(-OR^{10})_2$, in which Z is as defined above, and each of the groups represented by $R^{10}$, which may be the same or different, is a $C_1$–$C_6$ alkyl group.

In the compounds of formula (Ia), where $R^4$ represents an alkyl group, this may be a straight or branched chain group having from 1 to 20, preferably from 1 to 16 and more preferably from 1 to 5, carbon atoms, for example the methyl, ethyl, propyl, isopropyl, butyl, sec-butyl, t-butyl, pentyl, isopentyl, t-pentyl, hexyl, isohexyl, heptyl, nonyl, decyl, undecyl, dodecyl, tridecyl, tetradecyl, pentadecyl, hexadecyl, heptadecyl, octadecyl, nonadecyl and icosyl groups, preferably the methyl, ethyl, propyl, isopropyl, butyl, sec-butyl, t-butyl and pentyl groups.

Where $R^5$, $R^6$, $R^7$ or $R^{10}$ represents a $C_1$–$C_6$ alkyl group, it may be a straight or branched chain group and is preferably a $C_1$–$C_4$ alkyl group, such as methyl, ethyl, propyl, isopropyl, butyl, isobutyl or sec-butyl group, preferably a methyl, ethyl, propyl or isopropyl group. Where $R^8$ or $R^9$ represents a $C_1$–$C_6$ alkyl group, it may be one of these groups but, in this case, is preferably a methyl or ethyl, more preferably methyl, group.

Where $R^4$ represents a $C_2$–$C_{20}$ alkenyl group, this may be a straight or branched chain group having at least one carbon-carbon double bond. Examples include the vinyl, 1-propenyl, 2-propenyl, isopropenyl, 1-butenyl, 3-butenyl, 4-pentenyl, 1-methylvinyl, 5-hexenyl and 8-heptadecenyl groups. Such alkenyl groups may be unsubstituted or be substituted by a carboxy or esterified carboxy group, e.g. the 2-carboxyvinyl (cis or trans), 2-carboxy-1-propenyl (cis or trans) and 1-methyl-2-carboxyvinyl (cis or trans) groups.

Where $R^4$ represents a $C_3$–$C_8$ cycloalkyl group, this may be, for example, a cyclopropyl, cyclobutyl, cyclopentyl, cyclohexyl, cycloheptyl or cyclooctyl group.

Where $R^4$ or $R^8$ represents an optionally substituted aralkyl group, it may be any of the groups hereinbefore exemplified for $R^2$.

Where $R^4$ represents an optionally substituted phenyl group, the substituents are $C_1$–$C_6$ alkyl, halogen, nitro, carboxy or $C_2$–$C_7$ alkoxycarbonyl substituents. Examples of such groups represented by $R^4$ include the phenyl, o-tolyl, m-tolyl, p-tolyl, o-chlorophenyl, m-chlorophenyl, p-chlorophenyl, o-bromophenyl, m-bromophenyl, p-bromophenyl, p-nitrophenyl, o-carboxyphenyl, m-carboxyphenyl, p-carboxyphenyl, o-methoxycarbonylphenyl, m-methoxycarbonylphenyl, p-methoxycarbonylphenyl, o-ethoxycarbonylphenyl, m-ethoxycarbonylphenyl and p-ethoxycarbonylphenyl groups.

Where $R^6$, $R^7$, $R^8$ or $R^9$ represents an aryl group, it is preferably a phenyl, tolyl, o-chlorophenyl, m-chlorophenyl, p-chlorophenyl or trimethylphenyl (more preferably 2,4,6-trimethylphenyl) group.

Where $R^6$ or $R^7$ represents a $C_2$–$C_6$ alkenyl or alkynyl group, this may be a straight or branched chain group and examples include the vinyl, allyl, 1-propynyl, 2-propynyl and isopropenyl groups.

Where $R^8$ represents a group of formula —CH$_2$(—O—CO)$_m$—B, m is 0 or 1 and B is an oxygen-containing heterocyclic group. The heterocyclic group contains 5 or 6 ring atoms, of which at least one, and preferably 1 or 2, is an oxygen atom. The group may be unsubstituted or, if substituted, has at least one $C_1$–$C_4$ alkyl substituent. Examples of such groups represented by $R^8$ include the 2,2-dimethyl-1,3-dioxolan-4-ylmethyl and 3,4-dihydropyran-2-ylcarbonyloxymethyl groups.

Of the esters represented by formula (Ia), the preferred compounds are those in which $R^{2a}$ represents a $C_2$–$C_7$ alkanoyl group, a $C_2$–$C_7$ alkylcarbamoyl group, a ($C_1$–$C_6$ alkoxy)carbonylmethylcarbamoyl group, a $C_2$–$C_7$ alkoxycarbonyl group, a 2,2-dimethyl-1,3-dioxolan-4-ylmethylcarbonyl group, a $C_1$–$C_6$ alkanesulphonyl group, an arenesulphonyl group, a di($C_1$–$C_6$ alkoxy)phosphinyl group or a ($C_1$–$C_6$ alkoxy)-($C_1$–$C_6$ alkylthio)phosphinyl group.

Where $R^8$ represents a group derived by the removal of an omega-hydroxy group from an optionally protected sugar alcohol, the sugar alcohol may be, for example, glycerol, erythritol, threitol, arabinitol, adenitol, xylitol, sorbitol, mannitol or dulcitol. The protecting group or groups on such alcohols may be chosen from a wide variety of such groups and are not critical to the present invention. Examples of such groups include aliphatic acyl groups (such as the formyl or acetyl groups), cyclic ether groups (such as the tetrahydro-2-furanyl or tetrahydro-2-pyranyl groups), 1-alkoxyethyl groups (such as the 1-methoxyethyl or 1-ethoxyethyl groups) or silyl groups (such as the trimethylsilyl, triethylsilyl or dimethyl-t-butylsilyl groups). Alternatively, or in addition, the hydroxy groups at the 1- and 2-positions or the hydroxy groups at the 1- and 3-positions may be an alkylene, cycloalkylene or alkylidene group optionally having an aryl substituent, for example a methylene, ethylene, isopropylidene, benzylidene or cyclohexyline group. A particularly preferred such sugar alcohol group is the group derived from a pentaacetylglucose.

Preferred classes of compounds of the invention are:
1. Compounds of formula (I) and (Ia) where:
   X represents a chlorine or fluorine atom.
2. Compounds of formula (I) where:
   Y represents a group of formula =N—OH.
3. Compounds of formula (I) where:
   X represents a chlorine or fluorine atom; and
   Y represents a group of formula =N—OH.
4. Compounds of formula (Ia) where $R^{2a}$ represents:
   a group of formula —CO.NR$^6$R$^7$ where $R^6$ and $R^7$ are independently selected from the group consisting of hydrogen atoms and $C_1$–$C_6$ alkyl groups;
   a group of formula —COR$^4$ where $R^4$ represents a $C_1$–$C_{20}$ alkyl group, a benzyl group or a phenyl group; or
   a group of formula —COOR$^8$ where $R^8$ represents a $C_1$–$C_6$ alkyl group, a benzyl group or a phenyl group.
5. Compounds of formula (Ia) where $R^{2a}$ represents:
   a group of formula —CO.NR$^6$R$^7$ where $R^6$ and $R^7$ are independently selected from the group consisting of $C_1$–$C_4$ alkyl groups; or
   a group of formula —COR$^4$ where $R^4$ represents a $C_1$–$C_5$ alkyl group.
6. Compounds of formula (Ia) where $R^{2a}$ represents:
   a group of formula —CO.NR$^6$R$^7$ where $R^6$ and $R^7$ are independently selected from the group consisting of $C_1$ and $C_2$ alkyl groups; or a group of formula —COR$^4$ where $R^4$ represents a $C_1$–$C_3$ alkyl group.
7. Compounds of formula (Ia) where $R^{2a}$ represents a dimethylcarbamoyl group or a propionyl group.
8. Compounds as in any one of 4–7 above, where X represents a chlorine or fluorine atom.

The compounds of formula (I) and (Ia) can exist in the form of syn and anti isomers with respect to the nitrogen atom of the oxime group and the present invention is not limited to either isomer. The compounds may thus be in the form of the syn isomer, the anti isomer or a mixture thereof.

The configuration at the 13-position may be $\alpha$ or $\beta$. Thus, the compounds of the invention include both stereoisomers, 13$\alpha$ and 13$\beta$, and any mixture thereof. Most preferably, the compounds of the invention adopt the $\beta$-configuration at the 13-position.

Of all of the compounds of the invention, the derivatives of milbemycins A$_4$ and D [i.e. compounds of formulae (I) and (Ia) and salts and esters thereof where $R^1$ represents an ethyl or isopropyl group] are preferred.

Compounds of the invention may be prepared as illustrated in the following reaction scheme:

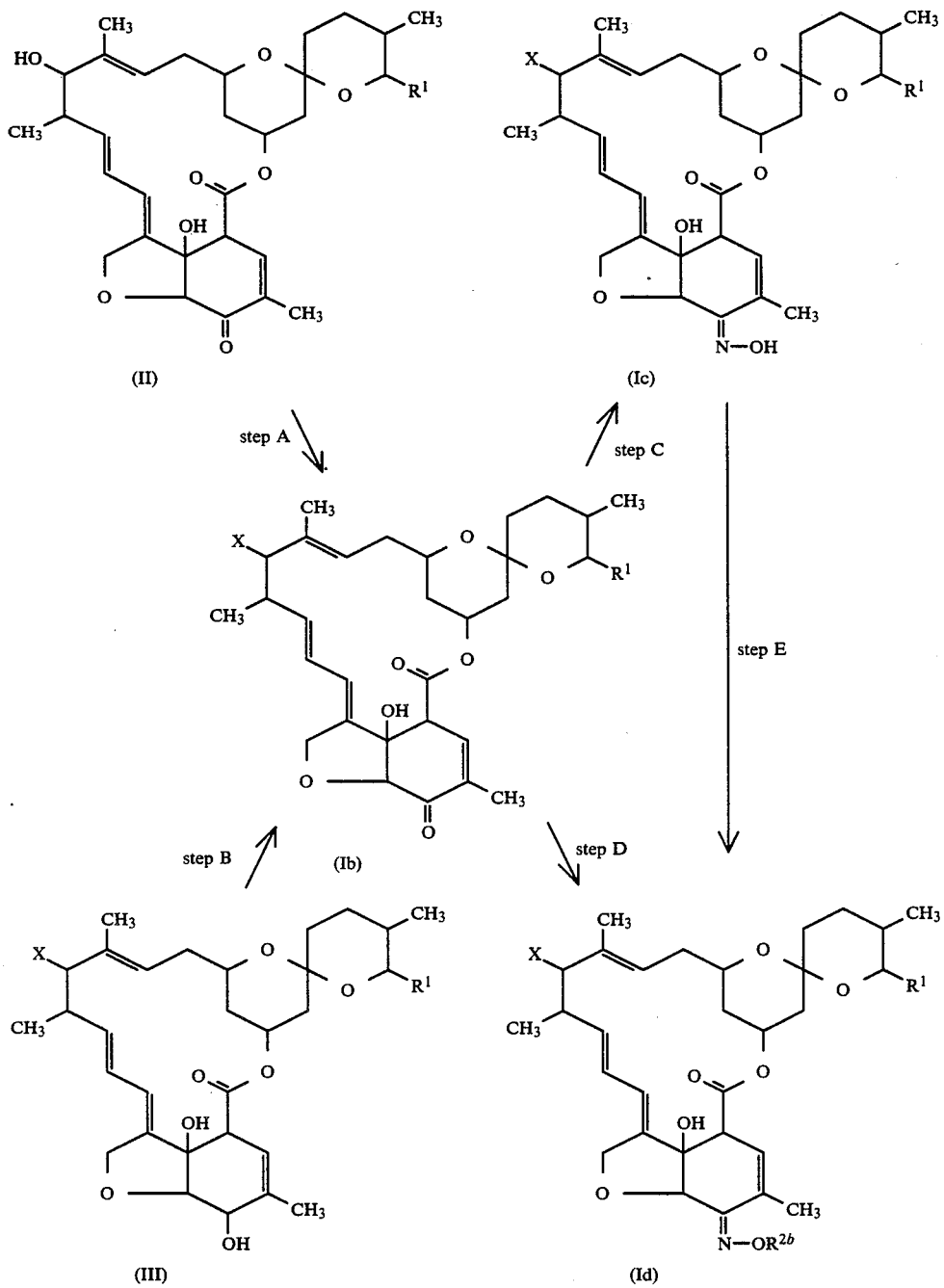

(II)  (Ic)  (Ib)  (III)  (Id)

In the above formulae, $R^1$, X and Y are as defined above. $R^{2b}$ represents any group which may be represented by $R^2$ or the acid residue of an ester, e.g. any group represents by $R^{2a}$.

Step A

In this step, a compound of formula (II) (which is a known compound, described, for example, in U.S. Pat. No. 4,423,209) is reacted with a halogenating agent to convert the hydroxy group at the 13-position to a halogen atom and yield the compound of formula (Ib).

There is no particular limitation upon the nature of the halogenating agent to be employed in this step, provided that it is capable of converting a hydroxy group on a macrolide compound to a halogen atom.

Examples of suitable halogenating agents include dimethylaminosulfur trifluoride, diethylaminosulfur trifluoride, phosphorus trichloride, thionyl chloride, phosphorus tribromide, thionyl bromide, bromotrimethylsilane, chlorotrimethylsilane/sodium iodide, methyl iodide/triphenyl phosphite and 2-chloro-3-ethylbenzoxazolium tetrafluoroborate/tetraethylammonium chloride.

The amount of halogenating agent is not critical, but we prefer to employ at least an equimolar amount with respect to the compound of formula (II), to ensure complete halogenation. A preferred ratio of halogenating agent to compound of formula (II) is from 1:1 to 10:1, more preferably from 1:1 to 4:1.

The halogenation reaction is preferably effected in the presence of a solvent, the nature of which is not critical, provided that it has no adverse effect upon the reaction. Suitable solvents include, for example: hydrocarbons, such as hexane, petroleum ether or benzene; halogenated hydrocarbons, particularly halogenated aliphatic hydrocarbons, such as chloroform or methylene chloride; amides, such as dimethylformamide; dimethyl sulfoxide; acetonitrile; and mixtures of any two or more of these solvents.

The reactions will take place over a wide range of temperatures and the precise reaction temperature chosen is not particularly critical. In general, we prefer to carry out the reaction at a temperature in the range of from −70° C. to +80° C. In the case of fluorination, a relatively low temperature within this range is preferred, for example from −60° C. to 0° C. For other halogenation, the reaction is more preferably carried out at room temperature or with slight heating.

The time required for the reaction may vary widely, depending upon many factors, notably the nature of the reagents and the reaction temperature; however, under the conditions suggested, a period of from 15 minutes to 1 day will normally suffice.

The compounds of formula (Ib) prepared in this step themselves have acaricidal, insecticidal and anthelmintic activities. They are, however, also important as intermediates to prepare compounds of formulae (Ic) and (Id), which have even stronger acaricidal, insecticidal and anthelmintic activities.

Step B

In this step, a compound of formula (III) is reacted with an oxidizing agent to convert the hydroxy group at the 5-position to a keto group and thus give the compound of formula (Ib). The compound of formula (III) used as a starting material in this step may be readily prepared by the method described in Tetrahedron Letters, 24 (48), 5333–5336. Specifically, a compound corresponding to the compound of formula (III), but in which the halogen atom X is replaced by a hydroxy group, is first produced with a suitable hydroxy-protecting group to protect only the hydroxy group at the 5-position. The hydroxy group at the 13-position is then halogenated with a suitable halogenating agent (e.g. as described in relation to Step A), and finally the hydroxy-protecting group at the 5-position is removed by conventional means.

Examples of suitable oxidizing agents for use in this step include activated manganese dioxide, chromium trioxide/pyridine and selenium dioxide.

Solvents and other reaction conditions, including reaction temperature, are as described hereafter for Step E.

Step C

In this step, the compound of formula (Ib) obtained as described in Step A or Step B, is reacted with hydroxylamine or with a salt thereof to give the oxime compound of formula (Ic).

Where a salt of hydroxylamine is employed, its nature is not critical, although we prefer to use salts with mineral acids, such as hydrochloric acid, nitric acid or sulfuric acid.

The reaction is preferably effected in the presence of a solvent, the nature of which is not critical, provided that it has no adverse effect upon the reaction. Examples of suitable solvents include: alcohols, such as methanol or ethanol; ethers, such as tetrahydrofuran or dioxane; aliphatic carboxylic acids, such as acetic acid; water, and mixtures of any two or more of these solvents.

The reaction will take place over a wide range of temperatures, and the precise reaction temperature chosen is not critical to the invention. We generally prefer to carry out the reaction at a temperature of from 10° to 80° C. The time required for the reaction may vary widely, depending upon many factors, notably the reaction temperature and the nature of the reagents; however, under the conditions suggested above, a period of from 1 hour to 1 day will normally suffice.

Step D

In this step, a compound of formula (Ib) is reacted with an oximating agent of formula $NH_2OR^{2b}$ (in which $R^{2b}$ is as defined above) or with a salt thereof (such as those described in Step C) to convert the keto group at the 5-position to an oxime group. The reaction is similar to that described in Step C and may be carried out under the same reaction conditions.

Step E

Alternatively, where $R^{2b}$ represents the residue of an acid $R^{2b}OH$, for example a carboxylic acid, an N,N-disubstituted carbamic acid, a carbonic acid, a sulfonic acid or a phosphonic acid, the compound of formula (Id) may be prepared by reacting an acid halide $R^{2b}X^1$ (in which $X^1$ represents a halogen atom, for example a chlorine or bromine atom) with the compound of formula (Ic), prepared as described in Step C. The reaction is preferably effected in the presence of a solvent and of an acid-binding agent.

The acid-binding agent is preferably a base and the nature thereof is not critical, provided that it does not have any adverse effect upon other parts of the molecule of the milbemycin derivative and that it is capable of binding with (and effectively removing from the reaction system) the acid produced in the course of the reaction. The base is preferably organic and examples of organic bases include triethylamine, N,N-dimethylaniline, pyridine, 4-dimethylaminopyridine, 1,4-diazabicyclo[2.2.0]octane, 1,5-diazabicyclo[4.3.0]nonene-5 and 1,8-diazabicyclo[5.4.0]undecene-7.

There is also no particular limitation upon the nature of the solvent, provided that it has no adverse effect upon the reaction. Examples of suitable solvents include: hydrocarbons, such as hexane, benzene, toluene and xylene; ethers, such as diethyl ether, tetrahydrofuran and dioxane; and halogenated hydrocarbons, particularly halogenated aliphatic hydrocarbons, such as methylene chloride, chloroform and carbon tetrachloride.

The reaction temperature is not particularly critical and we therefore generally find it convenient to carry out the reaction at about room temperature. The time required for the reaction may vary widely, depending upon many factors, notably the nature of the reagents and the reaction temperature; however, a period of from 30 minutes to 5 hours will normally suffice.

After completion of any of the above reactions, the desired product may be recovered from the reaction mixture by conventional means. For example, one suitable recovery technique comprises: pouring the reaction mixture into water; if necessary, removing insoluble materials by filtration; if necessary, neutralizing the mixture with an acid or a base; extracting the mixture with a water-immiscible organic solvent; and then drying the extract and distilling the solvent from it to leave the desired product. If required, this product may be further purified by such conventional techniques as recrystallization or the various chromatography techniques, particularly column chromatography.

The compound of formula (II) or the compound corresponding to compound (III) but in which X is replaced by a hydroxy group, which compounds are used as starting materials, may be derived from milbemycins which are fermentation products. Normally, the milbemycins are produced as mixtures of several compounds, the different compounds being produced at different rates. If desired, mixtures of such compounds may be subjected to the reactions described above or the individual compounds may be separated prior to such reaction.

Representative examples of compounds of the present invention are given in the following list.

1. 13-fluoro-5-ketomilbemycin $A_4$
2. 13-chloro-5-ketomilbemycin $A_4$
3. 13-bromo-5-ketomilbemycin $A_4$
4. 13-iodo-5-ketomilbemycin $A_4$
5. 13-fluoro-5-ketomilbemycin D
6. 13-chloro-5-ketomilbemycin D
7. 13-bromo-5-ketomilbemycin D
8. 13-iodo-5-ketomilbemycin D
9. 13-fluoro-5-ketomilbemycin $A_3$
10. 13-chloro-5-ketomilbemycin $A_3$
11. 13-bromo-5-ketomilbemycin $A_3$
12. 13-iodo-5-ketomilbemycin $A_3$
13. 13-fluoro-5-ketomilbemycin $A_4$ oxime
14. 13-chloro-5-ketomilbemycin $A_4$ oxime
15. 13-bromo-5-ketomilbemycin $A_4$ oxime
16. 13-iodo-5-ketomilbemycin $A_4$ oxime
17. 13-fluoro-5-ketomilbemycin D oxime
18. 13-chloro-5-ketomilbemycin D oxime
19. 13-chloro-5-ketomilbemycin D oxime
20. 13-iodo-5-ketomilbemycin D oxime
21. 13-fluoro-5-ketomilbemycin $A_3$ oxime
22. 13-chloro-5-ketomilbemycin $A_3$ oxime
23. 13-bromo-5-ketomilbemycin $A_3$ oxime
24. 13-iodo-5-ketomilbemycin $A_3$ oxime
25. 13-fluoro-5-ketomilbemycin $A_4$ 5-O-methyloxime
26. 13-fluoro-5-ketomilbemycin $A_3$ 5-O-methyloxime
27. 13-fluoro-5-ketomilbemycin $A_4$ 5-O-acetyloxime
28. 13-chloro-5-ketomilbemycin $A_4$ 5-O-acetyloxime
29. 13-fluoro-5-ketomilbemycin $A_4$ 5-O-(carboxymethyl)oxime
30. 13-fluoro-5-ketomilbemycin $A_3$ 5-O-(carboxymethyl)oxime
31. 13-chloro-5-ketomilbemycin $A_4$ 5-O-benzyloxime
32. 13-chloro-5-ketomilbemycin $A_3$ 5-O-benzyloxime
33. 13-fluoro-5-ketomilbemycin D 5-O-propionyloxime
34. 13-chloro-5-ketomilbemycin D 5-O-propionyloxime
35. 13-fluoro-5-ketomilbemycin $A_3$ 5-O-acetyloxime
36. 13-bromo-5-ketomilbemycin $A_3$ 5-O-valeryloxime
37. 13-bromo-5-ketomilbemycin $A_4$ 5-O-valeryloxime
38. 13-fluoro-5-ketomilbemycin $A_3$ 5-O-valeryloxime
39. 13-fluoro-5-ketomilbemycin $A_4$ 5-O-valeryloxime
40. 13-fluoro-5-ketomilbemycin $A_4$ 5-O-pivaloyloxime
41. 13-fluoro-5-ketomilbemycin $A_4$ 5-O-octanoyloxime
42. 13-fluoro-5-ketomilbemycin $A_3$ 5-O-octanoyloxime
43. 13-fluoro-5-ketomilbemycin $A_4$ 5-O-decanoyloxime
44. 13-chloro-5-ketomilbemycin D 5-O-hexadecanoyloxime
45. 13-fluoro-5-ketomilbemycin D 5-O-hexadecanoyloxime
46. 13-fluoro-5-ketomilbemycin $A_4$ 5-O-hexadecanoyloxime
47. 13-fluoro-5-ketomilbemycin $A_3$ 5-O-hexadecanoyloxime
48. 13-fluoro-5-ketomilbemycin $A_4$ 5-O-(ethoxycarbonyl)oxime
49. 13-chloro-5-ketomilbemycin D 5-O-(p-chlorophenoxycarbonyl)oxime
50. 13-fluoro-5-ketomilbemycin $A_4$ 5-O-(benzyloxycarbonyl)oxime
51. 13-fluoro-5-ketomilbemycin $A_4$ 5-O-(p-chlorobenzyloxycarbonyl)oxime
52. 13-fluoro-5-ketomilbemycin $A_4$ 5-O-(m-nitrobenzyloxycarbonyl)oxime
53. 13-fluoro-5-ketomilbemycin $A_4$ 5-O-(p-tolyloxycarbonyl)oxime
54. 13-fluoro-5-ketomilbemycin $A_4$ 5-O-(N,N-dimethylthiocarbamoyl)oxime
55. 13-fluoro-5-ketomilbemycin $A_4$ 5-O-(N,N-dimethylcarbamoyl)oxime
56. 13-chloro-5-ketomilbemycin $A_4$ 5-O-(N,N-dimethylcarbamoyl)oxime
57. 13-chloro-5-ketomilbemycin $A_4$ 5-O-(N-methylcarbamoyl)oxime
58. 13-chloro-5-ketomilbemycin D 5-O-(N,N-diallylcarbamoyl)oxime
59. 13-bromo-5-ketomilbemycin $A_3$ 5-O-(N-phenyl-N-methylcarbamoyl)oxime
60. 13-fluoro-5-ketomilbemycin $A_4$ 5-O-(p-toluenesulfonyl)oxime
61. 13-chloro-5-ketomilbemycin D 5-O-methanesulfonyloxime
62. 13-fluoro-5-ketomilbemycin $A_4$ 5-O-(O,O-diethylthiophosphono)oxime
63. 13-bromo-5-ketomilbemycin $A_3$ 5-O-benzoyloxime
64. 13-chloro-5-ketomilbemycin $A_4$ 5-O-(p-chlorobenzoyl)oxime
65. 13-fluoro-5-ketomilbemycin $A_4$ 5-O-(2,2-dimethyl-1,3-dioxolan-4-ylmethoxycarbonyl)oxime
66. 13-fluoro-5-ketomilbemycin $A_4$ 5-O-(3,4-dihydropyran-2-carbonyloxymethoxycarbonyl)oxime
67. 13-fluoro-5-ketomilbemycin D 5-O-methyloxime
68. 13-fluoro-5-ketomilbemycin D 5-O-acetyloxime
69. 13-chloro-5-ketomilbemycin D 5-O-acetyloxime
70. 13-chloro-5-ketomilbemycin D 5-O-benzyloxime
71. 13-fluoro-5-ketomilbemycin $A_4$ 5-O-propionyloxime
72. 13-chloro-5-ketomilbemycin $A_4$ 5-O-propionyloxime
73. 13-bromo-5-ketomilbemycin D 5-O-valeryloxime
74. 13-fluoro-5-ketomilbemycin D 5-O-valeryloxime
75. 13-fluoro-5-ketomilbemycin D 5-O-pivaloyloxime
76. 13-fluoro-5-ketomilbemycin D 5-O-octanoyloxime
77. 13-fluoro-5-ketomilbemycin D 5-O-decanoyloxime
78. 13-fluoro-5-ketomilbemycin D 5-O-(ethoxycarbonyl)oxime
79. 13-chloro-5-ketomilbemycin $A_4$ 5-O-(p-chlorophenoxycarbonyl)oxime
80. 13-fluoro-5-ketomilbemycin D 5-O-(benzyloxycarbonyl)oxime
81. 13-fluoro-5-ketomilbemycin D 5-O-(N,N-dimethylthiocarbamoyl)oxime
82. 13-fluoro-5-ketomilbemycin D 5-O-(N,N-dimethylcarbamoyl)oxime
83. 13-chloro-5-ketomilbemycin D 5-O-(N,N-dimethylcarbamoyl)oxime
84. 13-chloro-5-ketomilbemycin D 5-O-(N-methylcarbamoyl)oxime 85. 13-chloro-5-ketomilbemycin A$_4$ 5-O-(ethoxycarbonyl)oxime
86. 13-chloro-5-ketomilbemycin D 5-O-(ethoxycarbonyl)oxime Of the compounds listed above, preferred compounds are: Compounds Nos. 1, 2, 5, 6, 9, 10, 13, 14, 17, 18, 21, 22, 27, 28, 33, 34, 35, 38, 39, 40, 48, 49, 50, 54, 55, 56, 57, 68, 69, 71, 72, 74, 75, 78, 79 and 80, and the more preferred compounds are: Nos. 13, 14, 17, 18, 33, 34, 48, 55, 56, 71, 72, 78, 82, 83, 85 and 86 and the most preferred compounds are: Nos. 13, 14, 17, 18, 33, 34, 55, 56, 71, 72, 82 and 83, especially the 13$\beta$-isomers thereof and particularly:

13$\beta$-fluoro-5-ketomilbemycin D oxime
13$\beta$-fluoro-5-ketomilbemycin A$_4$ oxime
13$\beta$-chloro-5-ketomilbemycin D oxime
13$\beta$-chloro-5-ketomilbemycin A$_4$ oxime
13$\beta$-fluoro-5-ketomilbemycin D 5-O-(N,N-dimethylcarbamoyl)oxime
13$\beta$-fluoro-5-ketomilbemycin A$_4$ 5-O-(N,N-dimethylcarbamoyl)oxime
13$\beta$-chloro-5-ketomilbemycin D 5-O-(N,N-dimethylcarbamoyl)oxime
13$\beta$-chloro-5-ketomilbemycin A$_4$ 5-O-(N,N-dimethylcarbamoyl)oxime
13$\beta$-fluoro-5-ketomilbemycin D 5-O-propionyloxime
13$\beta$-fluoro-5-ketomilbemycin A$_4$ 5-O-propionyloxime
13$\beta$-chloro-5-ketomilbemycin D 5-O-propionyloxime
13$\beta$-chloro-5-ketomilbemycin A$_4$ 5-O-propionyloxime The compounds of the invention have a strong acaricidal activity against, for example, adults, imagos and eggs of Tetranychus, Panonychus and rust mites, which are parasitic to fruit trees, vegetables and flowers. They are also active against Ixodidac, Dermanyssidae and Sarcoptidae, which are parasitic to animals. Further, they are active against: exoparasites, such as Oestrus, Lucilia, Hypoderma, Gautrophilus, lice and fleas, which are parasitic to animals and birds, particularly livestock and poultry; domestic insects, such as cockroaches and houseflies; and various harmful insects in agricultural and horticultural areas, such as aphids and larval Lepidoptera. They are also effective against Meloidogyne in the soil, Bursaphelenchus and Phizoglyphus. They are also effective against insects of the orders Coleoptera, Homoptera, Heteroptera, Diptera, Thysanoptera, Orthoptera, Anoplura, Siphonaptera, Mallophage, Thysanura, Isoptera, Psocoptera, and Hymenoptera.

The compounds of the invention equally can be used to control other plant-damaging insects, particularly insects that damage plants by eating them. The compounds can be used to protect both ornamental plants and productive plants, particularly cotton (e.g. against *Spodoptera littoralis* and *Heliothis virescens*), as well as vegetable crops (e.g. against *Leptinotarsa decemlineata* and *Myzus persicae*) and rice crops (e.g. against *Chilo suppressalis* and Laodelphax).

The activity of the compounds of the invention is pronounced, both systemically and by contact. Accordingly, the compounds are very effective against sucking insects, especially sucking insects of the order Homoptera and most particularly the family Aphididae (such as *Aphis fabae, Aphis craccivora* and *Myzus persicae*), which are difficult to control with known compositions.

Accordingly, the compounds of the invention can be used to treat all manner of plants (as well as the seeds from which such plants are grown and the environment containing such plants) to protect them from insects such as those exemplified above. Such plants include cereals (e.g. maize or rice), vegetables (e.g. potatoes or soybeans), fruits and other plants (e.g. cotton).

The compounds of the invention can similarly be used to protect animals from a variety of ectoparasites, by applying the compounds to the animals or to the animals' environment, e.g. livestock housing, animal boxes, abattoirs, pasture land and other grasslands, as well as to any other places liable to be infested. The compounds may also be applied to external parts of the animals, preferably before they are infested.

Moreover, the compounds of the invention are effective against various parasitical helminths. These parasites can attack livestock, poultry and pet animals (such as pigs, sheep, goats, cows, horses, dogs, cats and fowl) and can cause grave economic damage. Among the helminths, the nematodes in particular often cause serious infection. Typical genera of nematodes which are parasitic on these animals and against which the compounds of the invention are effective include:

Haemonchus,
Trichostrongylus,
Ostertagia,
Nematodirus,
Cooperia,
Ascaris,
Bunostomum,
Oesophagostomum,
Chabertia,
Trichuris,
Strongylus,
Trichonema,
Dictyocaulus,
Capillaria,
Heterakis,
Toxocara,
Ascaridia,
Oxyuris,
Ancylostoma,
Uncinaria,
Toxascaris and
Parascaris.

Certain parasitical species of the genera Nematodirus, Cooperia and Oesophagostomum attack the intestines, while certain species of the genera Haemonchus and Ostertagia parasitize the stomach, and parasites belonging to the genus Dictyocaulas are found in the lungs. Parasites belonging to the families Filariidae and Setariidae are found in internal tissues and organs, for example, the heart, the blood vessels, the subcutaneous tissues and the lymphatic vessels. The compounds of the invention are active against all these parasites.

The compounds of the invention are also effective against parasites which infect humans. Typical of the parasites which may most commonly be found in the digestive tracts of human beings are parasites of the genera Ancylostoma, Necator, Ascaris, Strongyloides, Trichinella, Capillaria, Trichuris and Enterobius. The compounds are also active against parasites of the genera Wuchereria, Brugia, Onchocerca and Loa of the family Filariidae (which are found in blood, tissues and organs other than the digestive tract and are medically important), parasites of the genus Dracunculus and parasites of the genera Strongyloides and Trichinella, which especially infect the exointestinal canal.

The form of the compositions of the invention and the nature of the carriers or diluents employed in them will vary depending upon the intended use of the composition. For example, where the compounds of the invention are to be employed as anthelmintics, they are preferably administered orally, parenterally or topically and the form of compositions chosen will be appropriate to the intended route of administration.

For oral administration, the composition of the invention is preferably in the form of a liquid drink comprising a non-toxic solution or suspension, preferably aqueous, of the active compound in admixture with a suspending agent (such as bentonite), a wetting agent or other diluents. The drink, in general, also contains an anti-foaming agent. The active compound would normally be present in the drink in an amount of from 0.01 to 0.5% by weight, more preferably from 0.01 to 0.1% by weight.

Compositions for oral administration may also be in the form of dry solids, preferably in unit dosage form, such as capsules, pills or tablets containing the desired amount of the active compound. These compositions may be prepared by mixing the active compound uniformly with suitable diluents, fillers, disintegrators and/or binding agents, for example starch, lactose, talc, magnesium stearate and vegetable gum. The weight and contents of the preparation will vary widely, depending upon the nature of the animal to be treated, the degree of infection, the nature of the parasite and the body weight of the animal to be treated.

The compounds may also be administered as an additive to animal feedstuffs, in which case they may be dispersed uniformly in the feedstuffs, used as a top dressing or used in the form of pellets. The content of active compound in the feedstuff is preferably from 0.0001 to 0.02%, in order to achieve the desired anthelmintic activity.

For parenteral administration, the compound of the invention is preferably dissolved or suspended in a liquid vehicle, preferably a vegetable oil, such as peanut oil or cottonseed oil. Where the compound is a salt of a compound of formula (II), the liquid vehicle may be water or another aqueous medium. Depending upon the animal to be treated, the injection may be subcutaneous or into the proventriculus, a muscle or the trachea. Such preparations would normally contain the active compound at a concentration of from 0.05 to 50% by weight.

The compounds of the invention may also be administered topically in admixture with a suitable carrier, such as dimethyl sulphoxide or a hydrocarbon solvent. Such preparations would be applied directly to the outside of the animal by spraying (e.g. by a hand spray or in spray races), by dipping (e.g. in a plunge dip), by a pour-on solution or by manual methods (e.g. hand-dressing).

The dose of active compound may be varied, depending upon the nature of the animal to be treated, and the nature and degree of parasitic infection. However, best results for oral administration are achieved when the dose is from 0.01 to 100 mg, more preferably from 0.5 to 50 mg, per 1 kg body weight. The compound may be administered in a single dose or in divided doses for a relatively short period, such as from 1 to 5 days.

Where the composition of the invention is intended for agricultural or horticultural use, a variety of forms and formulations are possible. For example, it may be formulated as dusts, coarse dusts, soluble powders, microgranules, fine microgranules, wettable powders, dilute emulsions, emulsifiable concentrates, aqueous or oily suspensions or solutions (which may be directly sprayable or for dilution), aerosols or capsules in, for example, polymeric substances. The carrier employed may be natural or synthetic and organic or inorganic; it is generally employed to assist the active compound to reach the substrate to be treated, and to make it easier to store, transport or handle the active compound. Solid, liquid and gaseous carriers may be employed, chosen from carriers well known in the art for use with compositions of this type.

Such formulations may be prepared by conventional means, e.g. by intimate mixing and/or grinding of the active ingredient(s) with the carrier or diluent, e.g. solvent, solid carrier or, optionally, surface-active agent.

Suitable solvents include: aromatic hydrocarbons, preferably the $C_8$ to $C_{12}$ fractions from petroleum distillation, such as xylene mixtures or substituted naphthalenes; esters of phthalic acid, such as dibutyl or dioctyl phthalate; aliphatic hydrocarbons, such as cyclohexane or the paraffins; alcohols and glycols or esters thereof, such as ethanol, ethylene glycol, ethylene glycol monomethyl ether or ethylene glycol monoethyl ether; ketones, such as cyclohexanone; strongly polar solvents, such as N-methyl-2-pyrrolidone, dimethyl sulphoxide or N,N-dimethylformamide; optionally epoxidized vegetable oils, such as epoxidized coconut oil or soybean oil; and water.

Solid carriers, which may be used, for example, in dusts and dispersible powders, include natural mineral fillers, such as calcite, talc, kaolin, montmorillonite or attapulgite. In order to improve the physical properties of the composition, it is also possible to add highly dispersed silicic acid or highly dispersed absorbent polymers. Suitable granulated adsorptive carriers may be porous (such as pumice, ground brick, sepiolite or bentonite) or non-porous (such as calcite or sand). A wide variety of pregranulated materials, organic or inorganic, may also be used; examples include dolomite and ground plant residues.

Surface-active agents which may be used are well known in the art and may be non-ionic, cationic or anionic agents having good emulsifying, dispersing and wetting properties. Mixtures of such agents may also be used.

Compositions may also contain stabilizers, anti-foaming agents, viscosity regulators, binders or adhesives or any combination thereof, as well as fertilizers or other active substances to achieve special effects.

Pesticidal compositions will generally contain: from 0.01 to 99%, more preferably from 0.1 to 95%, by weight of the active compound; from 1 to 99.99% of a solid or liquid additive; and from 0 to 25%, more preferably from 0.1 to 25%, of a surface-active agent. Whereas commercial products are generally sold as concentrated compositions, they are generally diluted by the end-user to a concentration of from 0.001 to 0.0001% by weight (from 10 to 1 ppm).

The invention is further illustrated by the following Examples, of which Examples 1 to 25 illustrate the preparation of various compounds of the invention, Examples 26 to 28 demonstrate the activity of compounds of the invention. All separations by column chromatography were carried out by gradient elution in which the eluents were mixtures of hexane and ethyl acetate ranging from 10:1 to 2:1 by volume.

EXAMPLE 1

13β-Fluoro-5-ketomilbemycin A4 (Step A)

70 mg of diethylaminosulfur trifluoride were added dropwise to a solution of 560 mg of 13-hydroxy-5-ketomilbemycin A4 in 25 ml of methylene chloride, whilst cooling at −60° C., and the mixture was stirred for 15 minutes. At the end of this time, the reaction mixture was poured into water and extracted with ethyl acetate. The organic extract was dried over anhydrous sodium sulfate and concentrated by evaporation under reduced pressure. The residue was purified by silica gel column chromatography, to give 320 mg (yield 57%) of the title compound.

Infrared Absorption Spectrum (KBr) $\nu_{max}$ cm$^{-1}$: 3450, 1735, 1715, 1680.

Mass spectrum (m/z): 559 (M+), 541, 521.

Nuclear Magnetic Resonance Spectrum (CDCl$_{3j}$) δ ppm:
- 2.6 (1H, multiplet);
- 3.09 (1H, triplet of doublets, J=2, 6 & 10.1 Hz);
- 3.88 (1H, singlet);
- 4.02 (1H, singlet);
- 4.40 (1H, doublet of doublets, J=9.9 & 47.6 Hz);
- 4.75 (2H, multiplet);
- 5.2–5.5 (3H, multiplet);
- 5.75–5.9 (2H, multiplet);
- 6.54 (1H, multiplet).

EXAMPLE 2

13β-Chloro-5-ketomilbemycin A4 (Step A)

47 μl of thionyl chloride were added dropwise to a solution of 235 mg of 13-hydroxy-5-ketomilbemycin A4 in 40 ml of dry benzene, whilst ice-cooling, and the mixture was stirred at room temperature for 2 hours. The reaction mixture was then poured into water and then treated in the same manner as described in Example 1, to give 100 mg (yield 41%) of the title compound.

Mass spectrum (m/z): 574 (M+), 556, 538.

Nuclear Magnetic Resonance Spectrum (CDCl$_3$) δ ppm:
- 4.12 (1H, doublet, J=11.0 Hz);
- 4.75 (2H, multiplet);
- 4.95 (1H, multiplet);
- 5.2–5.5 (2H, multiplet);
- 5.7–5.9 (2H, multiplet);
- 6.54 (1H, multiplet).

EXAMPLE 3

13β-Bromo-5-ketomilbemycin A4 (Step A)

The procedure described in Example 2 was repeated, except that 280 mg of 13-hydroxy-5-ketomilbemycin A4 and 80 mg of phosphorus tribromide were used, to give 90 mg (yield 29%) of the title compound.

Infrared Absorption Spectrum (KBAr) $\nu_{max}$ cm$^{-1}$: 3450, 1715, 1680.

Nuclear Magnetic Resonance Spectrum (CDCl$_3$) δ ppm:
- 4.30 (1H, doublet, J=11.0 Hz);
- 5.2–5.5 (3H, multiplet);
- 5.75–5.90 (2H, multiplet);
- 6.54 (1H, multiplet).

EXAMPLE 4

13β-Iodo-5-ketomilbemycin A4 (Step A)

45 mg of trimethylsilyl chloride were added, under a nitrogen stream, to a solution of 194 mg of 13-hydroxy-5-ketomilbemycin A4 and 66 mg of sodium iodide in 15 ml of acetonitrile, and the mixture was stirred at room temperature for 8 hours. The reaction mixture was poured into water and then treated in the same manner as described in Example 1, to give 96 mg (yield 41%) of the title compound.

Infrared Absorption Spectrum (KBr) $\nu_{max}$ cm$^{-1}$: 3460, 1735, 1715, 1685.

Nuclear Magnetic Resonance Spectrum (CDCl$_3$) δ ppm:
- 3.06 (1H, triplet of doublets, J=2.6 & 9.5 Hz);
- 4.58 (1H, doublet, J=11.0 Hz).

EXAMPLE 5

13β-Fluoro-5-ketomilbemycin D (Step B)

0.60 g of activated manganese dioxide was added to a solution of 170 mg of 13-fluoromilbemycin D in 3 ml of methylene chloride at room temperature, and the mixture was vigorously stirred for 10 minutes. The reaction mixture was then filtered, and the insolubles were washed with methylene chloride. The filtrate and the washings were combined and concentrated by evaporation under reduced pressure. The residue was purified by silica gel column chromatography, to give 151 mg (yield 89%) of the title compound.

Mass spectrum (m/z): 573 (M+), 555.

EXAMPLE 6

13β-Fluoro-5-ketomilbemycin D oxime (Step C)

150 mg of 13β-fluoro-5-ketomilbemycin D (prepared as described in Example 5) and 36 mg of hydroxylamine hydrochloride were added to 3 ml of ethanol, and the mixture was stirred at 70° C. for 90 minutes. The reaction mixture was then cooled and concentrated by evaporation under reduced pressure. Benzene was added to the residue, and the water formed in situ was removed azeotropically. The residue was purified by silica gel column chromatography, to give 90 mg (yield 58%) of the title compound.

Mass spectrum (m/z): 587 (M+), 321, 274.

Nuclear Magnetic Resonance Spectrum (CDCl$_3$) δ ppm:
- 3.07 (1H, doublet of doublets, J=1.9 & 9.5 Hz);
- 4.40 (1H, doublet of doublets, J=10.0 & 47.6 Hz);
- 4.67 (1H, singlet).

EXAMPLE 7

13β-Chloro-5-ketomilbemycin D oxime (Steps B and C)

119 mg of 13-chloromilbemycin D and 0.80 g of an activated manganese dioxide were reacted in the same manner as described in Example 5 to give 13β-chloro-5-ketomilbemycin D. 47 mg of hydroxylamine hydrochloride were added to the reaction mixture and the whole mixture was treated in the same manner as described in Example 6, to give 97 mg (yield 80%) of the title compound.

Mass spectrum (m/z): 603 (M+).

Nuclear Magnetic Resonance Spectrum (CDCl$_3$) δ ppm:
- 3.07 (1H, doublet of doublets, J=2.0 & 9.5 Hz);
- 4.09 (1H, doublet, J=10.6 Hz);
- 4.67 (1H, singlet).

EXAMPLE 8

13$\beta$-Chloro-5-ketomilbemycin A$_3$ oxime (Steps B and C)

39 mg of 13-chloromilbemycin A$_3$, 0.10 g of activated manganese dioxide and 10 mg of hydroxylamine hydrochloride were reacted in the same manner as described in Example 7, to give 15 mg (yield 38%) of the title compound.

Mass spectrum (m/z): 575 (M$^+$), 557.

Nuclear Magnetic Resonance Spectrum (CDCl$_3$) $\delta$ ppm:
3.26 (1H, multiplet);
4.09 (1H, doublet, J=10.6 Hz);
4.67 (1H, singlet).

EXAMPLE 9

13$\beta$-Fluoro-5-ketomilbemycin A$_4$ oxime (Step C)

A solution of 268 mg of 13$\beta$-fluoro-5-ketomilbemycin A$_4$ (prepared as described in Example 1) in 4 ml of methanol and 4 ml of dioxane was added dropwise to a solution of 166 mg of hydroxylamine hydrochloride in 3 ml of water, and the mixture was stirred at room temperature for 8 hours. At the end of this time, the reaction mixture was poured into water and extracted with ethyl acetate. The extract was dried over anhydrous sodium sulfate and then concentrated by evaporation under reduced pressure. The residue was purified by column chromatography through silica gel, to give 182 mg (yield 66.4%) of the title compound.

Infrared absorption spectrum (KBr) $\nu_{max}$cm$^{-1}$:
3450, 1740, 1720, 1710.

Mass spectrum (m/z): 573 (M$^+$), 555, 540.

Nuclear Magnetic Resonance Spectrum (CDCl$_3$) $\delta$ppm:
3.95 (1H, singlet);
4.41 (1H, doublet of doublets, J=10.3 $\delta$47.6 Hz);
4.67 (1H, singlet);
7.73 (1H, singlet).

EXAMPLE 10

13$\beta$-Chloro-5-ketomilbemycin A$_4$ oxime (Step C)

103.8 mg of 13$\beta$-chloro-5-ketomilbemycin A$_4$ (prepared as described in Example 2) and 75 mg of hydroxylamine hydrochloride were treated in the same manner as described in Example 9, to give 63.4 mg (yield 59.5%) of the title compound.

Mass spectrum (m/z): 589 (M$^+$), 571.

Nuclear Magnetic Resonance Spectrum (CDCl$_3$) $\delta$ppm:
3.94 (1H, singlet);
4.09 (1H, doublet, J=10.3 Hz);
4.67 (1H, singlet);
7.91 (1H, singlet).

EXAMPLE 11

13$\beta$-Iodo-5-ketomilbemycin A$_4$ oxime (Step C)

68 mg of 13$\beta$-iodo-5-ketomilbemycin A$_4$ and 35 mg of hydroxylamine hydrochloride were treated in the same manner as described in Example 9, to give 48 mg (yield 69%) of the title compound.

Infrared absorption spectrum (KBr) $\nu_{max}$cm$^{-1}$:
3400, 1735, 1720, 1710.

Nuclear Magnetic Resonance Spectrum (CDCl$_3$) $\delta$ppm:
3.95 (1H, singlet);
4.58 (1H, doublet, J=11.0 Hz);
4.67 (1H, singlet);
7.86 (1H, singlet).

EXAMPLE 12

13$\beta$-Fluoro-5-ketomilbemycins A$_{4+3}$ 5-O-methyloxime (Step D)

129 mg of a 2.3:1 by weight mixture of 13$\beta$-fluoro-5-ketomilbemycins A$_4$ and A$_3$ and 115 mg of O-methylhydroxylamine hydrochloride were reacted in the same manner as described in Example 9, to give 108 mg (yield 80%) of the title compound.

Infrared absorption spectrum (KBr) $\nu_{max}$ cm$^{-1}$:
3470, 1715.

Nuclear Magnetic Resonance Spectrum (CDCl$_3$) $\delta$ppm:
3.91 (1H, singlet);
4.00 (3H, singlet);
4.40 (1H, doublet of doublets, J=9.9 & 48.0 Hz);
4.56 (1H, singlet).

EXAMPLE 13

13$\beta$-Fluoro-5-ketomilbemycins A$_{4+3}$ 5-O-carboxymethyloxime (Step D)

The procedure decribed in Example 12 was repeated, but using O-carboxymehylhydroxylamine hydrochloride, to obtain a 2.8:1 mixture of the title compounds.

Mass spectrum (m/z, A$_4$): 557 (M$^+$−74), 551 539, 525.

Nuclear Magnetic Resonance Spectrum (CDCl$_3$) $\delta$ppm:
4.42 (1H, doublet of doublets, J=9.7 & 47.5 Hz);
6.4 (1H, broad singlet).

EXAMPLE 14

13$\beta$-Fluoro-5-ketomilbemycin A$_{4+3}$ 5-O-benzyloxime (Step D)

The procedure described in Example 12 was repeated, but using O-benzylhydroxylamine hyrochloride, to obtain a 7.3:1 mixture of the title compounds.

Mass spectrum (m/z, A$_4$): 663 (M$^+$), 649, 605, 556.

Nuclear Magnetic Resonance Spectrum (CDCl$_3$) $\delta$ppm:
3.88 (1H, singlet);
4.40 (1H, doublet of doublets, J=9.5 & 47.5 Hz);
4.60 (1H, singlet).

EXAMPLE 15

13$\beta$-Chloro-5-ketomilbemycin A$_4$ 5-O-acetyloxime (Step E)

7.7 mg of 1,4-diazabicyclo[2.2.2]octane and 5.4 $\mu$l of acetyl chloride were added to a solutin of 40.5 mg of 13$\beta$-chloro-5-ketomilbemycin A$_4$ oxime (prepared as described in Example 10) in 1.5 ml of acetonitrile, and the mixture was stirred at room temperature for 6 hours. At the end of this time, the reaction mixture was poured into water and extracted with ethyl acetate. The extract was dried over anhyrous sodium sulfate and concentrated by evaporation under reduced pressure. The residue was purified by column chromatography through silica gel to give 33.5 mg (yield 77.2%) of the title compound.

Mass spectrum (m/z): 631 (M$^+$), 588.

Nuclear Magnetic Resonance Spectrum (CDCl$_3$) $\delta$ppm:
2.24 (3H, singlet);

3.93 (1H, singlet);
4.10 (1H, doublet, J=10.6 Hz);
4.60 (1H, singlet).

EXAMPLE 16

13β-Chloro-5-ketomilbemycin A$_4$
5-O-(N,N-dimethylcarbamoyl) oxime (Step E)

100 mg of 13β-chloro-5-ketomilbemycin A$_4$ oxime (prepared as described in Example 10) and 19 μl of N,N-dimethylcarbamoyl chloride were treated in the same manner as described in Example 15, to give 80.6 mg (yield 72%) of the title compound.

Mass spectrum (m/z): 536 (M$^+$ −124), 519, 501.

Nuclear Magnetic Resonance Spectrum (CDCl$_3$) δppm:
2.99 (6H, singlet);
3.94 (1H, singlet);
4.10 (1H, doublet, J=10.6 Hz);
4.57 (1H, singlet);
4.71 (2H, singlet).

EXAMPLE 17

13β-Chloro-5-ketomilbemycin A$_4$
5-O-(N-methylcarbamoyl) oxime (Step E)

0.30 ml of methyl isocyanate was added to a solution of 100 mg of 13β-chloro 5-ketomilbemycin A$_4$ oxime (prepared as described in Example 10) in 2 ml of tetrahydrofuran, and the mixture was allowed to stand for 8 hours, whilst kept sealed. At the end of this time, the solvent was distilled off under reduced pressure, to give 95.7 mg (yield 87%) of the title compound.

Mass spectrum (m/z): 589 (M$^+$ −57), 571.

Nuclear Magnetic Resonance Spectrum (CDCl$_3$) δppm:
2.93 (3H, doublet, J=4.7 Hz);
3.87 (1H, singlet);
4.09 (1H, doublet, J=10.6 Hz);
4.67 (1H, singlet).

EXAMPLE 18

13β-Fluoro-5-ketomilbemycin A$_4$
5-O-(N,N-dimethylcarbamoyl)oxime (Step E)

57 mg of 13β-fluoro-5-ketomilbemycin A$_4$ oxime (prepared as described in Example 9) and 12 μl of N,N-dimethylcarbamyl chloride were treated in the same manner as described in Example 15, to give 49 mg (yield 76%) of the title compound.

Mass spectrum (m/z): 644 (M$^+$), 626, 600, 582.

Nuclear Magnetic Resonance Spectrum (CDCl$_3$) δppm:
2.99 (6H, singlet);
3.96 (1H, singlet);
4.41 (1H, doublet of doublets, J=9.9 & 47.6 Hz);
4.57 (1H, singlet);
4.72 (2H, singlet).

EXAMPLE 19

13β-fluoro-5-ketomilbemycin A$_4$ 5-O-pivaloyloxime (Step E)

15 μl of triethylamine and 14 μl of pivaloyl chloride were added to a solution of 57 mg of 13β-fluoro-5-ketomilbemycin A$_4$ oxime (prepared as described in Example 9) in 10 ml of benzene, and the mixture was then stirred at room temperature for 3 hours. At the end of this time, the reaction mixture was treated in the same manner as described in Example 15, to give 52 mg (yield 79%) of the title compound.

Mass spectrum (m/z): 657 (M$^+$), 639, 574.

Nuclear Magnetic Resonance Spectrum (CDCl$_3$) δppm:
1.29 (9H, singlet);
3.99 (1H, singlet);
4.41 (1H, doublet of doublets, J=9.9 & 47.6 Hz);
4.57 (1H, singlet);
4.72 (2H, singlet).

EXAMPLE 20

13β-Fluoro-5-ketomilbemycins A$_{4+3}$
5-O-octanoyloxime (Step E)

The procedure described in Example 15 was repeated, but using octanoyl chloride and a mixture of 13β-fluoro-5-ketomilbemycins A$_{4+3}$ oxime (prepared following substantially the procedures of Example 9), to obtain a 2.0:1 mixture of the title compounds.

Mass spectrum (m/z, A$_4$): 699 (M$^+$), 685.

Nuclear Magnetic Resonance Spectrum (CDCl$_3$) δppm:
4.41 (1H, doublet of doublets, J=10.1 & 48.4 Hz);
4.58 (1H, singlet);
4.8 (1H, broad singlet).

EXAMPLE 21

13β-Fluoro-5-ketomilbemycins A$_{4+3}$
5-O-hexadecanoyloxime (Step E)

The procedure described in Example 15 was repeated, but using hexadecanoyl chloride and a mixture of 13β-fluoro-5-ketomilbemycins A$_{4+3}$ oxime (prepared following substantially the procedures of Example 9), to obtain a 1.0:1 mixture of the title compounds.

Mass spectrum (m/z, A$_4$): 811 (M$^+$).

Nuclear Magnetic Resonance Spectrum (CDCl$_3$) δppm:
3.95 (1H, singlet);
4.43 (1H, doublet of doublets, J=9.9 & 48.0 Hz);
4.58 (1H, singlet).

EXAMPLE 22

13β-Fluoro-5-ketomilbemycins A$_{4+3}$ 5-O-acetyloxime (Step E)

The procedure described in Example 15 was repeated, but using a mixture of 13β-fluoro-5-ketomilbemycins A$_{4+3}$ oxime (prepared following substantially the procedures of Example 9), to obtain a 1.8:1 mixture of the title compounds.

Mass spectrum (m/z, A$_4$): 615 (M$^+$).

Nuclear Magnetic Resonance Spectrum (CDCl$_3$) δppm:
3.96 (1H, singlet);
4.43 (1H, doublet of doublets, J=8.7 & 48.0 Hz);
4.60 (1H, singlet).

EXAMPLE 23

13β-Chloro-5-ketomilbemycin A$_4$ 5-O-propionyloxime

The procedure described in Example 15 was repeated, but using propionyl chloride, to obtain the title compound.

Mass spectrum (m/z): 645 (M$^+$), 589.

Nuclear Magnetic Resonance Spectrum (CDCl$_3$) δppm:
4.11 (1H, doublet, J=10.4 Hz);
4.61 (1H, singlet);

4.96 (1H, singlet).

EXAMPLE 24

13β-Fluoro-5-ketomilbemycin A$_4$
5-O-p-toluenesulfonyloxime (Step E)

The procedure described in Example 15 was repeated, but using 13β-fluoro-5-ketomilbemycin A$_4$ oxime (prepared as described in Example 9) and p-toluenesulfonyl chloride, to obtain the title compound.
Mass spectrum (m/z): 517 (M$^+$ −210), 503, 455.
Nuclear Magnetic Resonance Spectrum (CDCL$_3$) δppm:
244 (3H, singlet);
3.84 (1H, singlet);
4.42 (1H, doublet of doublets, J=10.0 & 47.2 Hz);
4.54 (1H, singlet).

EXAMPLE 25

13β-Fluoro-5-ketomilbemycin A$_4$
5-O-(pentaacetylgluconoyl)oxime (step E)

The procedure described in Example 15 was repeated, but using 13β-fluoro-5-ketomilbemycin A$_4$ oxime (prepared as described in Example 9) and pentaacetylgluconyl chloride, to obtain the title compound.
Mass spectrum (m/z): 615 (M$^+$ −346), 573.
Nuclear Magnetic Resonance Spectrum (CDCl$_3$) δppm:
3.90 (1H, singlet);
4.1–4.4 (5H, multiplet);
4.52 (1H, singlet).

EXAMPLE 26

Anthelmintic activity against Dirofilaria immitis

Dogs having a body weight of 8 to 17 kg, naturally infected by *Dirofilaria immitis*, were used as the test animals. Each dog was given orally or by subcutaneous injection sufficient of a composition prepared as described below to provide 0.05 mg of the test compound shown in Table 1 per kilogram body weight. The test compositions were prepared by blending 1.0 g of each of the test compounds with 0.1 g of 2,6-di-t-butyl-p-cresol, 10 ml of dimethylacetamide and sufficient polyethylene glycol (PEG-400) to bring the total volume to 100 ml. A sample of blood was drawn from each dog immediately prior to administration of the composition and then 7 days and 14 days after administration.

0.02 ml of the blood was stained with Giemsa solution and the number of microfilaria was counted microscopically and determined as an average over four glass slides. The results are reported in Table 1.

TABLE 1

| Compound of Example | Percent Reduction of Microfilaria | | | |
|---|---|---|---|---|
| | Oral Administration | | Subcutaneous injection | |
| | 7 Days | 14 Days | 7 Days | 14 Days |
| 8 | 93.8 | 54.9 | — | — |
| 9 | 69.0 | 31.4 | — | — |
| 10 | 64.8 | 79.9 | 99.8 | 100 |
| 19 | 93.7 | 92.9 | 76.2 | 55.2 |

EXAMPLE 27

Acaricidal effect against Boophilus microplus

Engorged female ticks of the species *Boophilus microplus* were fixed dorsally using double-sided adhesive tape on polyvinyl chloride panels in rows, each row containing 10 ticks. Each compound of Examples 7, 9 and 19 was tested as follows:

One series of ticks was treated by injection with doses of from 0.0005 μg to 5 μg of the test compound dissolved in 2 μl or 1 μl of solvent, per tick. The efficacy of the compound was evaluated by determining the IR$_{90}$ value, i.e. the dose preventing reproduction in 90% of the female ticks, 30 days after the treatment. On the basis of the IR$_{90}$ values, all of the compounds tested were effective in doses of from 0.005 to 0.05 μg per series of ticks.

EXAMPLE 28

Acaricidal activity against Tetranychus urticae

The primary leaves of plants of the species *Vigna sinensis* Savi were infected with organic phosphate-sensitive mites (*Tetranychus urticae*). One day after infection, the infested plants were sprayed, using a Mizuho rotary sprayer, with 7 ml of a test solution containing the compound under test at a concentration ranging from 0.3 to 30 ppm, at a rate of 3.5 mg of the test solution per 1 cm$^2$ of leaf. The plants were assessed after 3 days by examining adult mites, under a binocular microscope, to determine living and dead individuals. Two plants were used for each concentration and each test compound. The plants were kept during the test in greenhouse compartments at 25° C. The results are reported in Table 2.

TABLE 2

| Compound of Example | Percentage Mortality | | | |
|---|---|---|---|---|
| | 30 ppm | 10 ppm | 3 ppm | 1 ppm |
| 1 | 98 | — | 35 | — |
| 9 | — | 100 | 89 | 36 |
| 10 | — | 95 | 80 | 55 |
| 12 | — | 100 | 100 | 63 |
| 15 | — | 100 | 100 | 56 |
| 16 | — | 100 | 100 | 33 |
| 18 | — | 100 | 100 | 83 |
| 19 | — | 100 | 100 | 87 |
| 20 | — | 100 | 100 | 89 |
| 21 | — | 100 | 80 | 45 |
| 22 | — | 100 | 98 | 55 |
| 23 | — | 100 | 97 | 51 |
| Control 1 | 61 | — | 2 | — |
| Control 2 | 77 | — | 3 | — |
| Control 3 | 70 | — | 12 | — |
| Control 4 | — | 45 | 15 | — |

*Control 1: 5-ketomilbemycin A$_4$
Control 2: 5-ketomilbemycin A$_4$ oxime
Control 3: 5-ketomilbemycin A$_4$ 5-O-(N,N-dimethylcarbamoyl)oxime
Control 4: 5-ketomilbemycin A$_4$ 5-O-pivaloyloxime

We claim:

1. A milbemycin compound of formula (I):

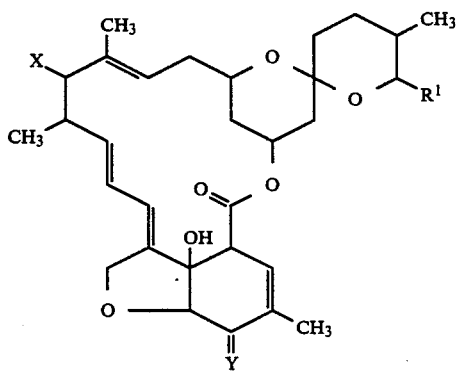

(I)

in which:
R[1] represents a methyl group, an ethyl group, an isopropyl group or a sec-butyl group;
X represents a halogen atom; and
Y represents an oxygen atom or a group of formula =N—OR[2], wherein
R2 represents a hyrogen atom, a $C_1$-$C_6$ alkyl group, a $C_7$-$C_9$ phenylalkyl group, a $C_7$-$C_9$ phenylalkyl group having at least one substituent on the phenyl ring selected from the group consisting of $C_1$-$C_6$ alkyl, halogen and nitro substituents or a group of formula —CH$_2$COOR[3], in which R[3] represents a hydrogen atom or a $C_1$-$C_6$ alkyl group;

and, when R[2] represents a hydrogen atom, a salt or ester thereof.

2. A compound as claimed in claim 1, wherein X represents a chlorine or fluorine atom.

3. A compound as claimed in claim 1, wherein Y represents a group of formula =N—OH.

4. A compound as claimed in claim 1, wherein:
X represents a chlorine or fluorine atom; and
Y represents a group of formula =N—OH.

5. A milbemycin compound of formula (Ia):

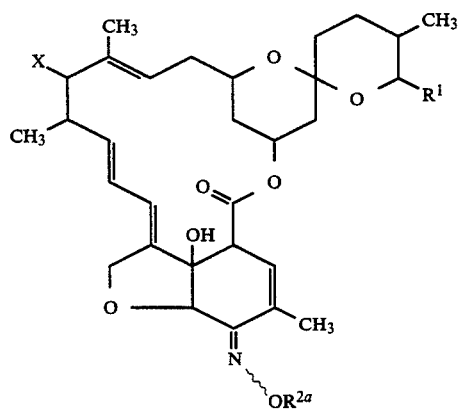

(Ia)

wherein:
R[1] represents a methyl group, an ethyl group, an isopropyl group or a sec-butyl group;
X represents a halogen atom; and
R[2a] represents:
a group of formula —COR[4], in which R[4] represents a $C_1$-$C_{20}$ alkyl group, a $C_2$-$C_{20}$ alkenyl group, a $C_3$-$C_8$ cycloalkyl group, a $C_7$-$C_9$ phenylalkyl group, a $C_7$-$C_9$ phenylalkyl group having at least one substituent on the phenyl ring selected from the group consisting of $C_1$-$C_6$ alkyl, halogen and nitro substituents, a phenyl group, a phenyl group having at least one substituent selected from the group consisting of $C_1$-$C_6$ alkyl, halogen, nitro, carboxy and $C_2$-$C_7$ alkoxycarbonyl substituents or a group of formula —(CH$_2$)$_n$COOR[5], wherein n is an integer from 1 to 3 and R[5] represents a hydrogen atom or a $C_1$-$C_6$ alkyl group;

a group of formula —CZ.NR[6]R[7], wherein R[6] and R[7] are the same or different and each represents a hydrogen atom, a $C_1$-$C_6$ alkyl group, a $C_2$-$C_6$ alkenyl group, a $C_2$-$C_6$ alkynyl group, a phenyl group or a phenyl group having at least one substituent selected from the group consisting of $C_1$-$C_6$ alkyl and halogen and Z represents an oxygen or sulfur atom;

a group of formula —COOR[8], wherein R[8] represents: a $C_1$-$C_6$ alkyl group; a $C_7$-$C_9$ phenylalkyl group, a $C_7$-$C_9$ phenylalkyl group having at least one substituent on the phenyl ring selected from the group consisting of $C_1$-$C_6$ alkyl, halogen and nitro substituents; a phenyl group; a phenyl group having at least one substituent selected from the group consisting of $C_1$-$C_6$ alkyl and halogen; a group of formula —CH$_2$(—O—CO)$_m$—B where m is 0 or 1 and B represents an oxygen-containing heterocyclic group having 5 or 6 ring atoms or said heterocyclic group having at least one $C_1$-$C_4$ alkyl substituent; or a group derived by removing an omega-hydroxy group from a sugar alcohol selected from the group consisting of glycerol, erythritol, threitol, arabinitol, adenitol, xylitol, sorbitol, mannitol and dulcitol or said sugar alcohol being protected by a group selected from the group consisting of formyl, acetyl, tetrahydro-2-furanyl, tetrahydro-2-pyranyl, 1-methoxyethyl, 1-ethoxyethyl, trimethylsilyl, triethylsilyl and dimethyl-t-butylsilyl;

a group of formula —SO$_2$R[9], wherein R[9] represents a $C_1$-$C_6$ alkyl group, a phenyl group, or a phenyl group having at least one substituent selected from the group consisting of $C_1$-$C_6$ alkyl and halogen; or a group of formula —(Z=)P(—OR[10])$_2$, in which Z is as defined above, and each of the groups represented by R[10], which may be the same or different, is a $C_1$-$C_6$ alkyl group.

6. A compound as claimed in claim 5, wherein X represents a chlorine or fluorine atom.

7. A compound as claimed in claim 5, where R[2a] represents:
a group of formula —CO.NR[6]R[7] where R[6] and R[7] are independently selected from the group consisting of hydrogen atoms and $C_1$-$C_6$ alkyl groups;
a group of formula —COR[4] where R[4] represents a $C_1$-$C_{20}$ alkyl group, a benzyl group or a phenyl group; or a group of formula —COOR[8] where R[8] represents a $C_1$-$C_6$ alkyl group, a benzyl group or a phenyl group.

8. A compound as claimed in claim 5, where R[2a] represents:
a group of formula —CO.NR[6]R[7] where R[6] and R[7] are independently selected from the group consisting of $C_1$-$C_4$ alkyl groups; or
a group of formula —COR[4] where R[4] represents a $C_1$-$C_5$ alkyl group.

9. A compound as claimed in claim 5, where R[2a] represents:

a group of formula —CO.NR⁶R⁷ where R⁶ and R⁷ are independently selected from the group consisting of $C_1$ and $C_2$ alkyl groups; or a group of formula —COR⁴ where R⁴ represents a $C_1$–$C_3$ alkyl group.

10. A compound as claimed in claim 9, where X represents a chlorine or fluorine atom.

11. A compound as claimed in claim 5, where $R^{2a}$ represents a dimethylcarbamoyl group or a propionyl group.

12. A compound as claimed in claim 1, wherein R¹ represents an ethyl or isopropyl group.

13. A compound as claimed in claim 5, wherein R¹ represents an ethyl or isopropyl group.

14. A compound as claimed in claim 9, wherein R¹ represents an ethyl or isopropyl group.

15. The compound as claimed in claim 1, which is 13β-fluoro-5-ketomilbemycin D oxime or a salt thereof.

16. The compound as claimed in claim 1, which is 13β-fluoro-5-ketomilbemycin A₄ oxime or a salt thereof.

17. The compound as claimed in claim 1, which is 13β-chloro-5-ketomilbemycin D oxime or a salt thereof.

18. The compound as claimed in claim 1, which is 13β-chloro-5-ketomilbemycin A₄ oxime or a salt thereof.

19. The compound as claimed in claim 5, which is 13β-fluoro-5-ketomilbemycin D 5-O-(N,N-dimethylcarbamoyl)oxime.

20. The compound as claimed in claim 5, which is 13β-fluoro-5-ketomilbemycin A₄ 5-O-(N,N-dimethylcarbamoyl)oxime.

21. The compound as claimed in claim 5, which is 13β-chloro-5-ketomilbemycin D 5-O-(N,N-dimethylcarbamoyl)oxime.

22. The compound as claimed in claim 5, which is 13β-chloro-5-ketomilbemycin A₄ 5-O-(N,N-dimethylcarbamoyl)oxime.

23. The compound as claimed in claim 5, which is 13β-fluoro-5-ketomilbemycin D 5-O-propionyloxime.

24. The compound as claimed in claim 5, which is 13β-fluoro-5-ketomilbemycin A₄ 5-O-propionyloxime.

25. The compound as claimed in claim 5, which is 13β-chloro-5-ketomilbemycin D 5-O-propionyloxime.

26. The compound as claimed in claim 5, which is 13β-chloro-5-ketomilbemycin A₄ 5-O-propionyloxime.

27. An anthelmintic, acaricidal and insecticidal composition comprising an active compound in admixture with a pharmaceutically, agriculturally or horticulturally acceptable carrier or diluent, wherein said active compound is selected from the group consisting of milbemycin compounds of formula (I):

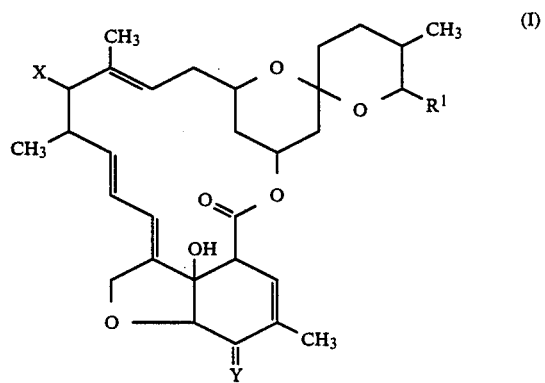

in which:
R¹ represents a methyl group, an ethyl group, an isopropyl group or a sec-butyl group;
X represents a halogen atom; and
Y represents an oxygen atom or a group of formula =N—OR², wherein
R2 represents a hydrogen atom, a $C_1$–$C_6$ alkyl group, a $C_7$–$C_9$ phenylalkyl group, a $C_7$–$C_9$ phenylalkyl group having at least one substituent on the phenyl ring selected from the group consisting of $C_1$–$C_6$ alkyl, halogen and nitro substituents or a group of formula —CH₂COOR³, in which R³ represents a hydrogen atom or a $C_1$–$C_6$ alkyl group;
and, when R² represents a hydrogen atom, a salt or ester thereof.

28. A composition as claimed in claim 27, wherein X represents a chlorine or fluorine atom.

29. A composition as claimed in claim 27, wherein Y represents a group of formula =N—OH.

30. A composition as claimed in claim 27, wherein:
X represents a chlorine or fluorine atom; and
Y represents a group of formula =N—OH.

31. An anthelmintic, acaricidal and insecticidal composition comprising an active compound in admixture with a pharmaceutically, agriculturally or horticulturally acceptable carrier or diluent, wherein said active compound is selected from the group consisting of milbemycin compounds of formula (Ia):

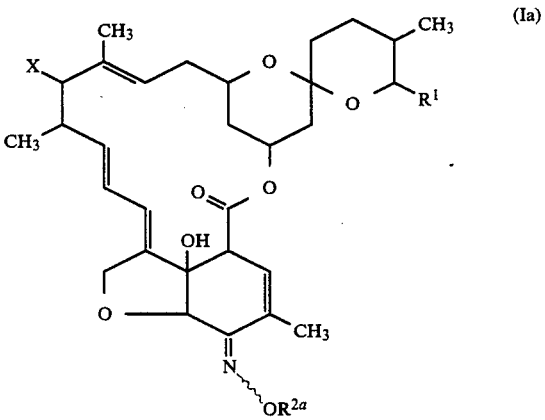

wherein:
R¹ represents a methyl group, an ethyl group, an isopropyl group or a sec-butyl group;
X represents a halogen atom; and $R^{2a}$ represents:

a group of formula —COR⁴, in which R⁴ represents a $C_1$-$C_{20}$ alkyl group, a $C_2$-$C_{20}$ alkenyl group, a $C_3$-$C_8$ cycloalkyl group, a $C_7$-$C_9$ phenylalkyl group, a $C_7$-$C_9$ phenylalkyl group having at least one substituent on the phenyl ring selected from the group consisting of $C_1$-$C_6$ alkyl, halogen and nitro substituents, a phenyl group, a phenyl group having at least one substituent selected from the group consisting of $C_1$-$C_6$ alkyl, halogen, nitro, carboxy and $C_2$-$C_7$ alkoxycarbonyl substituents or a group of formula —$(CH_2)_n COOR^5$, wherein n is an integer from 1 to 3 and $R^5$ represents a hydrogen atom or a $C_1$-$C_6$ alkyl group;

a group of formula —$CZ.NR^6R^7$, wherein $R^6$ and $R^7$ are the same or different and each represents a hydrogen atom, a $C_1$-$C_6$ alkyl group, a $C_2$-$C_6$ alkenyl group, a $C_2$-$C_6$ alkynyl group, a phenyl group or a phenyl group having at least one substituent selected from the group consisting of $C_1$-$C_6$ alkyl and halogen and Z represents an oxygen or sulfur atom;

a group of formula —$COOR^8$, wherein $R^8$ represents: a $C_1$-$C_6$ alkyl group; a $C_7$-$C_9$ phenylalkyl group, a $C_7$-$C_9$ phenylalkyl group having at least one substituent on the phenyl ring selected from the group consisting of $C_1$-$C_6$ alkyl, halogen and nitro substituents; a phenyl group; a phenyl group having at least one substituent selected from the group consisting of $C_1$-$C_6$ alkyl and halogen; a group of formula —$CH_2(-O-CO)_m$—B where m is 0 or 1 and B represents an oxygen-containing heterocyclic group having 5 or 6 ring atoms or said heterocyclic group having at least one $C_1$-$C_4$ alkyl substituent; or a group derived by removing an omega-hydroxy group from a sugar alcohol selected from the group consisting of glycerol, erythritol, threitol, arabinitol, adenitol, xylitol, sorbitol, mannitol and dulcitol or said sugar alcohol being protected by a group selected from the group consisting of formyl, acetyl, tetrahydro-2-furanyl, tetrahydro-2-pyranyl, 1-methoxyethyl, 1-ethoxyethyl, trimethylsilyl, triethylsilyl and dimethyl-t-butylsilyl;

a group of formula —$SO_2R^9$, wherein $R^9$, wherein $R^9$ represents a $C_1$-$C_6$ alkyl group, a phenyl group, or a phenyl group having at least one substituent selected from the group consisting of $C_1$-$C_6$ alkyl and halogen; or a group of formula —$(Z=)P(-OR^{10})_2$, in which Z is as defined above, and each of the groups represented by $R^{10}$, which may be the same or different, is a $C_1$-$C_6$ alkyl group.

32. A composition as claimed in claim 31, wherein X represents a chlorine or fluorine atom.

33. A composition as claimed in claim 31, where $R^{2a}$ represents:

a group of formula —$CO.NR^6R^7$ where $R^6$ and $R^7$ are independently selected from the group consisting of hydrogen atoms and $C_1$-$C_6$ alkyl groups;

a group of formula —COR⁴ where R⁴ represents a $C_1$-$C_{20}$ alkyl group, a benzyl group or a phenyl group; or a group of formula —$COOR^8$ where $R^8$ represents a $C_1$-$C_6$ alkyl group, a benzyl group or a phenyl group.

34. A composition as claimed in claim 31, where $R^{2a}$ represents:

a group of formula —$CO.NR^6R^7$ where $R^6$ and $R^7$ are independently selected from the group consisting of $C_1$-$C_4$ alkyl groups; or a group of formula —COR⁴ where R⁴ represents a $C_1$-$C_5$ alkyl group.

35. A composition as claimed in claim 31, where $R^{2a}$ represents:

a group of formula —$CO.NR^6R^7$ where $R^6$ and $R^7$ are independently selected from the group consisting of $C_1$ and $C_2$ alkyl groups; or a group of formula —COR⁴ where R⁴ represents a $C_1$-$C_3$ alkyl group.

36. A composition as claimed in claim 35, where X represents a chlorine or fluorine atom.

37. A composition as claimed in claim 31, where $R^{2a}$ represents a dimethylcarbamoyl group or a propionyl group.

38. A composition as claimed in claim 27, wherein $R^1$ represents an ethyl or isopropyl group.

39. A composition as claimed in claim 31, wherein $R^1$ represents an ethyl or isopropyl group.

40. A composition as claimed in claim 35, wherein $R^1$ represents an ethyl or isopropyl group.

41. A method of treating an animal parasitized by a parasite selected from the group consisting of helminths, acarids and insects, which comprises applying to or administering to said animal an active compound, wherein said active compound is selected from the group consisting of compounds of formula (I), as defined in claim 1, and salts and esters thereof.

42. A method of protecting animals or plants from damage by parasites selected from the group consisting of acarids, helminths and insects, which comprises applying an active compound to said animals, said plants or to seeds of said plants, or to a locus including said animals, said plants or said seeds, wherein said active compound is selected from the group consisting of compounds of formula (I), as defined in claim 1, and salts and esters thereof.

43. A composition as claimed in claim 27, wherein said active compound is 13β-fluoro-5-ketomilbemycin D oxime or a salt thereof.

44. A composition as claimed in claim 27, wherein said active compound is 13β-fluoro-5-ketomilbemycin $A_4$ oxime or a salt thereof.

45. A composition as claimed in claim 27, wherein said active compound is 13β-chloro-5-ketomilbemycin D oxime or a salt thereof.

46. A composition as claimed in claim 27, wherein said active compound is 13β-chloro-5-ketomilbemycin $A_4$ oxime or a salt thereof.

47. A composition as claimed in claim 31, wherein said active compound is 13β-fluoro-5-ketomilbemycin D 5-O-(N,N-dimethylcarbamoyl)oxime.

48. A composition as claimed in claim 31, wherein said active compound is 13β-fluoro-5-ketomilbemycin $A_4$ 5-O-(N,N-dimethylcarbamoyl)oxime.

49. A composition as claimed in claim 31, wherein said active compound is 13β-chloro-5-ketomilbemycin D 5-O-(N,N-dimethylcarbamoyl)oxime.

50. A composition as claimed in claim 31, wherein said active compound is 13β-chloro-5-ketomilbemycin $A_4$ 5-O-(N,N-dimethylcarbamoyl)oxime.

51. A composition as claimed in claim 31, wherein said active compound is 13β-fluoro-5-ketomilbemycin D 5-O-propionyloxime.

52. A composition as claimed in claim 31, wherein said active compound is 13β-fluoro-5-ketomilbemycin $A_4$ 5-O-propionyloxime.

53. A composition as claimed in claim 31, wherein said active compound is 13β-chloro-5-ketomilbemycin D 5-O-propionyloxime.

54. A composition as claimed in claim 31, wherein said active compound is 13β-chloro-5-ketomilbemycin $A_4$ 5-O-propionyloxime.

* * * * *

UNITED STATES PATENT AND TRADEMARK OFFICE
CERTIFICATE OF CORRECTION

PATENT NO. : 4,945,105

DATED : July 31, 1990

INVENTOR(S) : SATO et al

It is certified that error appears in the above-identified patent and that said Letters Patent is hereby corrected as shown below:

```
Title Page:
Section [56] References Cited, insert under
"U.S. PATENT DOCUMENTS":

--4,093,629  6/1978.....Fischer--

Column 29, lines 42-43 (Claim 31):

Delete "wherein R9" (second occurance).
```

Signed and Sealed this

Eighth Day of September, 1992

Attest:

DOUGLAS B. COMER

Attesting Officer     Acting Commissioner of Patents and Trademarks